United States Patent
Schock et al.

(10) Patent No.: US 6,238,382 B1
(45) Date of Patent: May 29, 2001

(54) INTRA-AORTIC BALLOON CATHETER HAVING A TAPERED Y-FITTING

(75) Inventors: Robert Schock, Sparta; Boris Leschinsky, Waldwick; Jeffrey McGinley, Lincoln Park, all of NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/377,477

(22) Filed: Aug. 19, 1999

(51) Int. Cl.[7] .................. A61M 25/16; A61M 25/18; A61M 39/00; A61M 39/10
(52) U.S. Cl. .................................................. 604/533
(58) Field of Search ................. 604/27, 48, 93.01, 604/96.01, 171, 174, 177, 264, 523, 525, 97.01, 98.01, 103.05, 533, 284

(56) References Cited

U.S. PATENT DOCUMENTS

| 5,217,439 | * | 6/1993 | McClusky . | |
| 5,695,467 | * | 12/1997 | Miyata et al. | 604/96 |

* cited by examiner

*Primary Examiner*—Sharon Kennedy
*Assistant Examiner*—Catherine Serke
(74) *Attorney, Agent, or Firm*—Abraham Ronai

(57) ABSTRACT

An intra-aortic balloon catheter system comprising an intra-aortic balloon catheter having a reduced gas path length, a protective sleeve, and a Y-fitting connector connecting the proximal end of the catheter to an intra-aortic balloon pump. The protective sleeve is disposed about at least a portion of the connector between a proximal and distal end of the connector.

11 Claims, 2 Drawing Sheets

INTRA-AORTIC BALLOON CATHETER HAVING A TAPERED Y-FITTING

BACKGROUND OF THE INVENTION

1. Field of the Invention

The invention relates to an intra-aortic balloon catheter. More particularly, the invention relates to an improved intra-aortic balloon catheter Y-fitting and sleeve guard.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body and is connected to a Y-fitting. A passageway for inflating and deflating the balloon extends through the catheter and is connected via the Y-fitting to an external pump. The patient's central aortic pressure is used to time the balloon and the patient's ECG may be used to trigger balloon inflation in synchronous counterpulsation to the patient's heart beat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

Intra-aortic balloon catheters may also have a passageway or lumen which can be used to measure aortic pressure. In this dual lumen construction, the central lumen may also be used to accommodate a guide wire to facilitate placement of the catheter and to infuse fluids, or to do blood sampling.

Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon. Other dual lumen intra-aortic balloon catheters have their central tube embedded or affixed to the inner surface of the outer tube.

The proximal end of the IAB catheter is connected to the pump by a connector, generally a Y-fitting. A sleeve is generally disposed about the exposed portion of the catheter to resist contamination of the catheter. Y-fittings presently on the market have a flat distal face which connects to a proximal end of the sleeve.

All IAB catheters have two opposing design considerations. On the one hand, it is desirable to make the outer diameter of the entire catheter as small as possible: to facilitate insertion of the catheter into the aorta, maximizing blood flow past the inserted catheter, and to allow for the use of a smaller sheath to further maximize distal flow. On the other hand, however, it is desirable to make the inner diameter of the outer tube as large as possible because a large gas path area is required to accomplish the rapid inflation and deflation of the balloon. As a result of these opposing design considerations there is a need for a smaller catheter with a larger gas path area.

A decrease in gas path length also would allow for a decrease in the diameter of the catheter. Design work has generally not focused on altering the gas path length because a catheter with minimal insertable length, given patient anatomy, is absolutely necessary to perform IAB therapy. The present invention decreases the gas path length not by decreasing the insertable length of IAB catheter tube but rather by introducing an innovative catheter-to-pump connector having a tapered distal end.

A Y-fitting connector having a tapered distal end allows the protective sleeve to be at least partially, and preferably entirely, disposed about the connector. Moving at least a portion of the sleeve over the connector eliminates the need for at least a portion of the uninserted section of the catheter, and thus, allows for an overall reduction in length of the catheter without altering the insertable length.

While the IAB catheters presently on the market may be suitable for the particular purpose employed, or for general use, they would not be as suitable for the purposes of the present invention as disclosed hereafter.

SUMMARY OF THE INVENTION

It is an object of the invention to produce an improved reduced diameter IAB catheter.

It is another object of the invention to produce an improved IAB catheter having a reduced length of restrictive gas path.

It is a further object of the invention to produce an improved IAB catheter-to-pump connector and a modified stat-guard seal.

The invention is an intra-aortic balloon catheter system comprising an intra-aortic balloon catheter having a reduced restrictive gas path length, a protective sleeve, and a Y-fitting connector connecting the proximal end of the catheter to an intra-aortic balloon pump. The protective sleeve is disposed about at least a portion of the connector between a proximal and distal end of the connector.

The elements of the present invention are not limited to intra-aortic balloon catheters. It may be desirable to employ elements of the present invention in other catheters and devices, having connectors and protective sheaths, where speed and efficiency of transferring a substance through the catheter is a design concern, such as but not limited to heart pumps.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
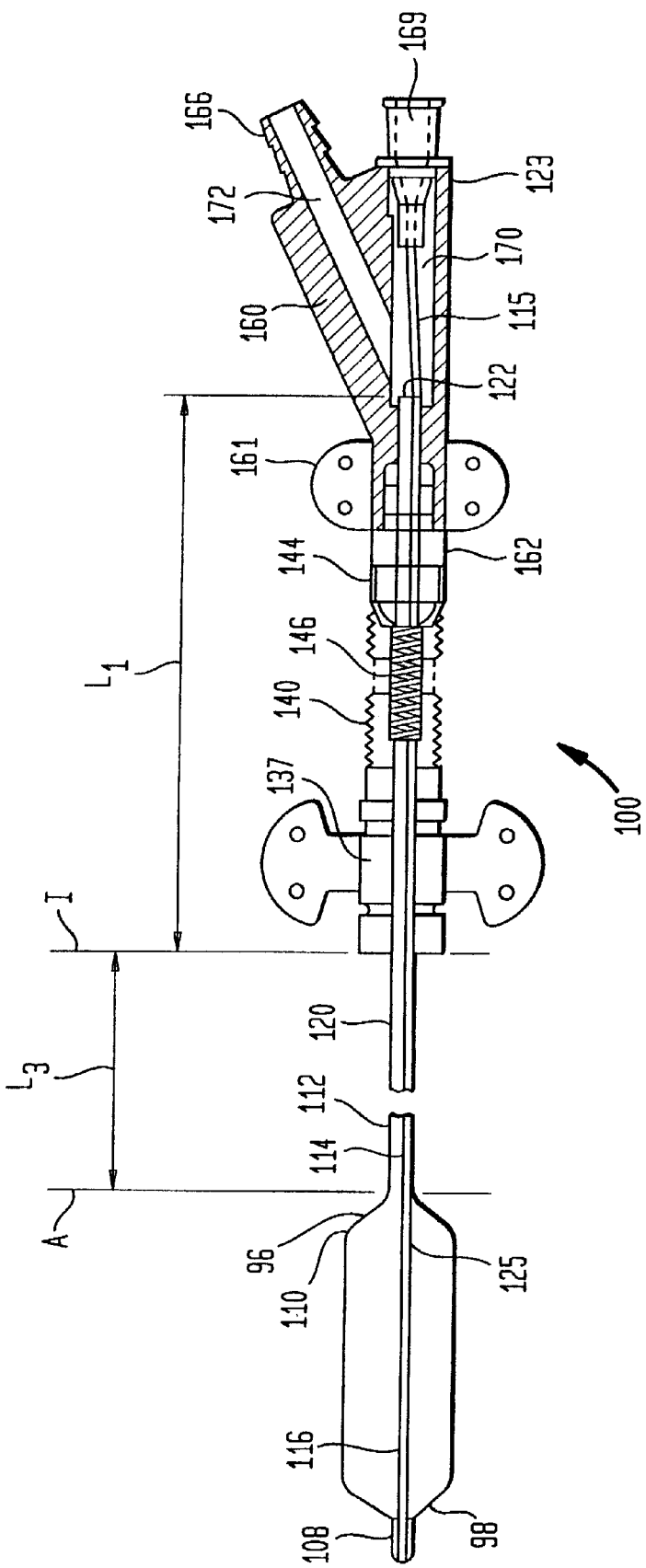
FIG. 1 is longitudinal cross sectional view of a prior art intra-aortic balloon catheter connected on its proximal end to a Y-fitting.

FIG. 1 illustrates a longitudinal cross sectional view of a prior art intra-aortic balloon catheter, generally designated 100, inserted at line I into the body of a patient (not shown). The intra-aortic balloon catheter 100 comprises a dual lumen catheter 120, a Y-fitting 160, a stat-guard body 137 having ears 161, a stat-guard sleeve 140, a balloon membrane 110, and a tip 108. The dual lumen catheter 120 comprises an outer gas tube 112 and an inner tube 114. A distal end 116 of the inner tube 114 is connected to the tip 108. A distal end 121 of the gas tube 112 is connected to a proximal end 96 of the balloon membrane 110. A distal end 98 of the balloon membrane 110 is connected to the tip 108. The stat-guard body 137 and the stat-guard sleeve 140 form a single unit and are disposed about dual lumen catheter 120. The purpose of the stat-guard sleeve 140 is to protect the uninserted portion of the dual lumen catheter 120 (to the right of line I) from contamination. A ring 144 connects the stat-guard sleeve 140 to a distal end 162 of the Y-fitting 160. The Y-fitting 160 comprises an inner tube lumen 170 and a communicating outer tube lumen 172. A proximal end 122 of the gas tube 112 is disposed within the inner tube lumen 170, for approximately a one inch length, and connected to a distal end 162 of the Y-fitting 160. A proximal end 115 of the inner tube is disposed within the inner tube lumen 170 of the Y-fitting 160 and is connected to a Y-fitting guide wire luer connector 169. The inner tube lumen 170 runs from the distal end 162 of the y-fitting 160 to a first proximal end 123 of the Y-fitting 160.

Inflation and deflation of the balloon membrane 110 is accomplished through the gas outer tube 112. The inner tube 114 can accommodate a guide wire for placement of the dual lumen catheter 120. When the guide wire is not disposed in the inner tube 114, the inner tube 114 may be used for measuring blood pressure in the descending aorta. This pressure measurement may be used to coordinate the inflation and deflation of the balloon membrane 110 with the pumping of the heart, however, use of the patient's ECG is preferred. Additionally, the inner tube 114 may be used to infuse liquids into the descending aorta, or to sample blood. Measurement of aortic pressure and blood sampling may be done through the proximal end 115 of the inner tube 114.

A strain-relief spring 146 is disposed about the dual lumen catheter 120 at the distal end of the Y-fitting 162. The proximal end 122 of the outer gas tube 121 communicates with the outer tube lumen 172 which terminates in a Y-fitting gas connector 166. The Y-fitting gas connector 166 may be connected to an intra-aortic balloon pump.

The portion of the outer gas tube 112 between line I and line A, having a length of L3, is inserted into a patient. Length L1 designates the uninserted portion of the outer gas tube 112.

Figure 2:
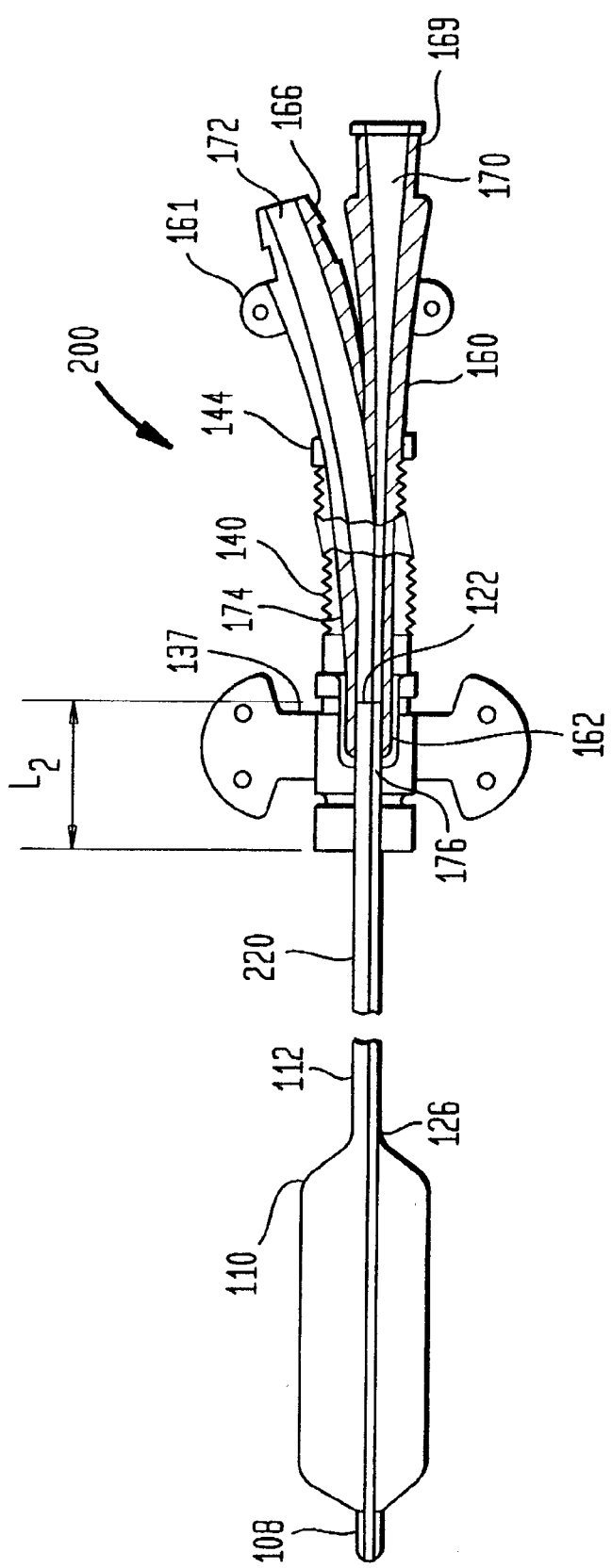
FIG. 2 is a longitudinal cross section view of the catheter of the present invention.

FIG. 2 illustrates an embodiment of the improved IAB catheter 200 inserted at Line I into the body of a patient (not shown).

The primary difference between the prior art IAB catheter 100 and the IAB catheter 200 of the present invention comprises the positioning of the stat-guard body 137 and the stat-guard sleeve 140 and the configuration and geometry of the Y-fitting 160. The Y-fitting 160 has a tapered distal portion 174, an inner tube lumen 170, and an outer tube lumen 172. At least a portion of the stat-guard sleeve 140 is disposed about the Y-fitting 160. Ring 144, or another appropriate member, connects the stat-guard sleeve 140 to the Y-fitting 160. The stat-guard body 137 and the stat-guard sleeve 140 are connected end-to-end to form a single unit. The tapered distal portion 174 is at least partially disposed within a Y-fitting lumen 176 in the stat-guard body 137. Another important difference between the prior art IAB catheter 100 and the improved IAB catheter 200 involves the reduced length of the gas outer tube 112 disposed within the Y-fitting 160. Reduction of the length of the gas outer tube 112 disposed within the Y-fitting 160 (FIG. 2) allows for a Y-fitting 160 having a gas flow path that is larger, and thus less restrictive, than that of the gas outer tube 112. The cross sectional area of the outer tube lumen 172 (FIG. 2) is on average larger than the cross sectional area of the gas outer tube 112. Thus, limiting the length the gas flows in the gas outer tube 112 by terminating the gas outer tube at the distal end 162 of the Y-fitting 160 results in a less restrictive gas flow path. The gas outer tube 112 is disposed within the outer tube lumen 172 of the connector 160 for a length of less than approximately one inch, preferably only a quarter of an inch.

Tapering the distal portion 174 of the Y-fitting 160, or alternatively simply reducing its size relative to the Y-fitting sleeve attachment ring 144 and the Y-fitting lumen 176, allows the stat-guard sleeve 140 and the stat-guard body 137 to be disposed about the Y-fitting 160. As a result, the Y-fitting can be moved closer to the insertion site (line I). Since the inserted length of the dual lumen catheter 120, L3, remains constant, the entire length of the dual lumen catheter 120 can be reduced. Tapering the distal portion 174 of the Y-fitting 160 also obviates the need for strain-relief spring 146 as the reduction of wall thickness in this area, coupled with a correctly chosen semi-flexible polymer material, results in increased flexibility.

Suture ears 161 project from a proximal portion of the Y-fitting. Suture ears 161 have been moved proximally as much as possible, as compared to the prior art Y-fitting 160, so as to allow the stat-guard sleeve 140 to be disposed over the Y-fitting for the greatest length possible. Note that it is anticipated to vary the shape and number of the suture ears 161.

The length, L3, of the inserted portion of the outer gas tube 112 between line I and line A is the same as in the prior art intra-aortic balloon catheter 100. The length, L2, between line I, the insertion point into the body of a patient, and the proximal end 122 of the outer gas tube 112 is less than the corresponding length, L1, in the prior art intra-aortic balloon catheter 100 illustrated in FIG. 1. The overall length of the intra-aortic balloon catheter 200 of the present invention is shorter than the prior art intra-aortic balloon catheter 100. The decreased length of the intra-aortic balloon catheter 200, specifically the reduced length of the uninserted portion of the intra-aortic balloon catheter 200, results in increased balloon inflation and deflation speeds, thus, allowing for a reduction in the diameter of the dual lumen catheter 120. Note that this reduction in diameter is not illustrated in FIG. 2.

What is claimed is:

1. An intra-aortic balloon catheter system comprising an intra-aortic balloon catheter, a protective sleeve, and a connector having proximal and distal ends, for connection between a proximal end of the catheter and a pump, said protective sleeve is at least partially slidingly disposed, and removeably connectable about the connector between the proximal end of the connector and a distal end connection with the catheter.

2. The intra-aortic balloon catheter system as claimed in claim 1 wherein the intra-aortic balloon catheter comprises an inner tube, defining an inner lumen, and an outer gas tube, defining an outer gas tube lumen and wherein the connector has a first lumen that communicates with the inner lumen and a second lumen that communicates with the outer gas tube lumen.

3. The intra-aortic balloon catheter system as claimed in claim 1 wherein the connector further comprises one or more suture ears projecting from a proximal portion of the connector.

4. The intra-aortic balloon catheter system as claimed in claim 1 wherein the connector has a proximal portion and a distal portion and wherein the distal portion of the connector is more flexible than the proximal portion.

5. The intra-aortic balloon catheter system as claimed in claim 2 wherein a proximal end of the outer gas tube is disposed for a length less than approximately 1 inch within the second lumen of the connector.

6. The intra-aortic balloon catheter as claimed in claim 2 wherein a proximal end of the outer gas tube is disposed for a length less than or equal to approximately ¼ of an inch within the second lumen of the connector.

7. A catheter system comprising an intra-aortic balloon catheter, a protective sleeve, and a Y-shaped connector for connection between a proximal end of the catheter and a pump, said protective sleeve is at least partially slidingly disposed about the intra-aortic balloon catheter and the connector between a proximal end and a distal end of the connector, a proximal end of the protective sleeve is connected to the connector, at least a portion of the connector has a taper toward the distal end of the connector, the intra-aortic balloon catheter comprises an inner lumen and an outer gas lumen, the connector has a first lumen that communicates with the inner lumen, a second lumen that communicates with the outer gas lumen, and suture ears that project from a proximal portion of the connector.

8. The intra-aortic balloon catheter system as claimed in claim 1 wherein the protective sleeve has a proximal end, said proximal end being removably connected to a point on the connector at least one quarter inch from the distal end of the connector.

9. The intra-aortic balloon catheter system as claimed in claim 1 wherein the protective sleeve has a proximal end, said proximal end being removably connected to a point on the connector at least one half inch from the distal end of the connector.

10. The catheter system as claimed in claim 7 where in the proximal end of the protective sleeve is removably connected to a point on the catheter at least one quarter inch from the distal end of the connector.

11. The intra-aortic balloon catheter system as claimed in claim 1 wherein the connector has a proximal portion and a distal portion and wherein the distal portion has a taper rendering it more flexible than the proximal portion.

\* \* \* \* \*